(12) United States Patent
Greenwood et al.

(10) Patent No.: US 11,886,950 B2
(45) Date of Patent: Jan. 30, 2024

(54) SYSTEM AND METHOD FOR ASSESSING AND VERIFYING THE VALIDITY OF A TRANSACTION

(71) Applicant: Healthcare Integrated Technologies Inc., Knoxville, TN (US)

(72) Inventors: Kenneth M. Greenwood, Davenport, FL (US); Scott Michael Boruff, Knoxville, TN (US); Jurgen Vollrath, Sherwood, OR (US)

(73) Assignee: Healthcare Integrated Technologies Inc., Knoxville, TN (US)

( * ) Notice: Subject to any disclaimer, the term of this patent is extended or adjusted under 35 U.S.C. 154(b) by 0 days.

(21) Appl. No.: 17/390,642

(22) Filed: Jul. 30, 2021

(65) Prior Publication Data
US 2022/0036018 A1 Feb. 3, 2022

Related U.S. Application Data

(60) Provisional application No. 63/103,416, filed on Aug. 3, 2020.

(51) Int. Cl.
| | | |
|---|---|---|
| *G06K 7/10* | (2006.01) | |
| *G06K 7/14* | (2006.01) | |
| *G16H 10/60* | (2018.01) | |
| *G06N 3/08* | (2023.01) | |
| *G16H 40/20* | (2018.01) | |
| *G16H 20/10* | (2018.01) | |
| *G16H 50/20* | (2018.01) | |

(52) U.S. Cl.
CPC ....... *G06K 7/10297* (2013.01); *G06K 7/1413* (2013.01); *G06N 3/08* (2013.01); *G16H 10/60* (2018.01); *G16H 20/10* (2018.01); *G16H 40/20* (2018.01); *G16H 50/20* (2018.01)

(58) Field of Classification Search
CPC .......................... G06K 7/10297; G06K 7/1413
USPC .......................................................... 235/451
See application file for complete search history.

(56) References Cited

U.S. PATENT DOCUMENTS

| | | | | |
|---|---|---|---|---|
| 11,416,874 | B1* | 8/2022 | Scotney | G06Q 50/18 |
| 11,437,126 | B2* | 9/2022 | Culbertson | H04L 63/1433 |
| 2020/0345299 | A1* | 11/2020 | Goldsmith | G16H 50/20 |
| 2020/0381106 | A1* | 12/2020 | Limaye | A61B 5/0004 |
| 2021/0110924 | A1* | 4/2021 | Tkach | G16H 20/70 |
| 2021/0267555 | A1* | 9/2021 | Janssen | G16H 40/20 |
| 2021/0393486 | A1* | 12/2021 | Choudhury | A61J 7/0076 |
| 2022/0101999 | A1* | 3/2022 | Bonutti | A61N 1/3605 |
| 2022/0115129 | A1* | 4/2022 | Baronov | G16H 50/20 |

\* cited by examiner

*Primary Examiner* — Ahshik Kim
(74) *Attorney, Agent, or Firm* — Jurgen Vollrath

(57) ABSTRACT

A method and system for validating compliance with the terms of a transaction, includes gathering sensor and human-sourced data and analyzing and grading the data for compliance with each element and with the transaction as a whole.

20 Claims, 3 Drawing Sheets

SYSTEM AND METHOD FOR ASSESSING AND VERIFYING THE VALIDITY OF A TRANSACTION

FIELD OF THE INVENTION

The present invention relates to transactions between two or more people, and verifying that the terms and inherent norms for compliance have been met.

BACKGROUND OF THE INVENTION

Most interactions between people can be defined in terms of one or more transactions. These may involve the transfer, use, or consumption of goods or materials. They may also include services that are to be performed. Or they may include both the transfer of materials and the provision of services.

At the end of such a transaction or during the course of a transaction, a party may question compliance with a part or the whole of the transaction. Parties to a transaction or third parties may inquire whether the transaction occurred, or is occurring in accordance with agreed upon terms or in accordance with inherent or expected norms. For instance, there may be an inquiry into whether the correct, intended, or a substantially equivalent material was transferred, or whether the services are being performed according to the specifications agreed upon or in accordance with commonly-accepted standards of service. The execution of such transactions can be of significant importance and can even result in the loss of life, if not done according to the agreed upon terms or accepted norms. For example, due to the untimely administration of medication, or due to the administration of incorrect medication by a nurse to a patient or resident of a nursing home. In the case of a surgical operation performed by a physician, the critical question may be whether the procedure was incorrectly performed, or performed in a manner not previously agreed upon, or not in compliance with the standards and norms expected in the particular industry. Or a transaction may result in significant loss of revenue, as in the case of the operation of controls by a machine operator, or in the running of an oil rig, which results in a fire or explosion, or in the case of the operator of a commercial motor vehicle, causing an accident or delivering goods to the wrong destination resulting in loss of time and added expense.

SUMMARY OF THE INVENTION

A system for validating transactions that involve interactions with a user, comprising a database for storing elements of a transaction, details about the participants, and compliance details for compliance with the elements of the transaction, at least two sensors for gathering transaction data between at least a first time and a second time, a processor, and a memory that includes machine-readable code defining an algorithm executable by the processor for analyzing data, including data from at least a first sensor to verify compliance with the compliance details and for corroborating compliance or lack of compliance by analyzing data from at least a second sensor for corroboration of the data from the first sensor.

The algorithm may define an artificial intelligence (AI) system configured to identify anomalies in the data captured by at least one sensor.

The anomalies in the data may include at least one of, anomalies in the data captured from a sensor over time during a transaction timespan, anomalies in sensor data compared to prior data captured for the user for previous transactions, and anomalies in sensor data compared to similar sensor data gathered under similar conditions for other users. The transaction timespan may include timespans before the first time and after the second time.

The data captured for analysis may include data provided by people, including one or more of: the user, other parties to the transaction, and parties peripherally associated with the transaction.

The machine-readable code may include logic for capturing and storing the data provided by people, including at least one of documentation and recordings related to the transaction.

The sensor data and data provided by people may include visual data, audio data, and other perceptual data.

The sensor data may include one or more of radar array recordings, audio recordings, video recordings, time records of events, compliance data captured by systems, temperature data, radio-frequency sensor array data, video and still photography camera data, streaming and still thermal camera data, monaural and stereo microphone data, sonar sensor data, ultrasonic sensor data, and subsonic sensor data.

The machine-readable code may include logic for authenticating one or more people forming part of a transaction, the system including data captured from one or more of, image capture devices operating in one or more frequency ranges, RFID tags, bar codes, identification cards, retina scans, facial recognition, voice print, tattoos (visible or invisible), and genetic code.

The transaction data captured by the system may include one or more of: types of materials involved in the transaction, quantity of material, any changes to those materials during the transaction, and the tracking of the movement of such materials.

The database may include one or more of: local storage using an SSD or RAID array, a distributed database or cloud system, and storage as rows in tables in a relational database.

The machine-readable code may include logic for defining the level of compliance with an element of a transaction or a transaction as a whole and for generating an alert in the event of the compliance value falling below a defined value or based on the detection of an anomaly.

The transaction data may include one or more of: facial expression, body posture, body movement, and vocal attributes data, and wherein the AI system is configured to assess the demeanor or emotional state of one or more participants in the transaction. The transaction data from the sensors is parsed to define symbolic representations to facilitate a more efficient interpretation by the AI system, wherein the conversion of sensor data into a symbolic representation includes passing the data through one or more parsers to extract specific types of information from a data stream.

Further, according to the invention, there is provided a method of verifying transactions involving interactions with a user, comprising defining the elements of a transaction, identifying the compliance details defining compliance with one or more of the elements of a transaction, capturing data from sensor- and human-provided data sources, and using an algorithm to analyze the data, verify compliance with one or more elements of a transaction, and corroborate the compliance or lack of compliance by comparing two or more of the data sources.

The algorithm may comprises an AI network, and may include logic to compare data from multiple data sources for the same time frame or related time-frames.

The analyzing of the data may include identifying at least one of: the physical state, and the emotional state of one or more of, the user, and other parties involved in the transaction.

The method may further comprise identifying emergency situations and notifying one or more parties in response to the identification. It may also include keeping a record of transactions and details about users and other parties to transactions, and may include generating reports in response to one or more of: identification of compliance or non-compliance with elements of a transaction, anomalies detected in the data from one or more of the data sources, defined events, and authorized requests.

The method may further include defining the degree of compliance according to a grading scale.

DETAILED DESCRIPTION OF THE INVENTION

In real life, during the transfer or conveyance of materials or performance of services, there are often many facets to consider; it is not always clear if such a transaction has been successfully performed, or performed to a required specification or standard, or meets any or all or the parties' expectations.

Even if recorded automatically and electronically, it is often not a clear yes/no answer if material has been conveyed and/or a service has been performed completely, successfully and satisfactorily, and if it complied with regulations governing the conveyance or the performance of the services. Performance is often measured subjectively in terms of quality, or may be graded in terms of degree of performance, or level of acceptance. Such measurements may be on a scale, for example from 1-100, or a percentage completion, or number of stars awarded based on level of the recipient's satisfaction.

Figure 1:
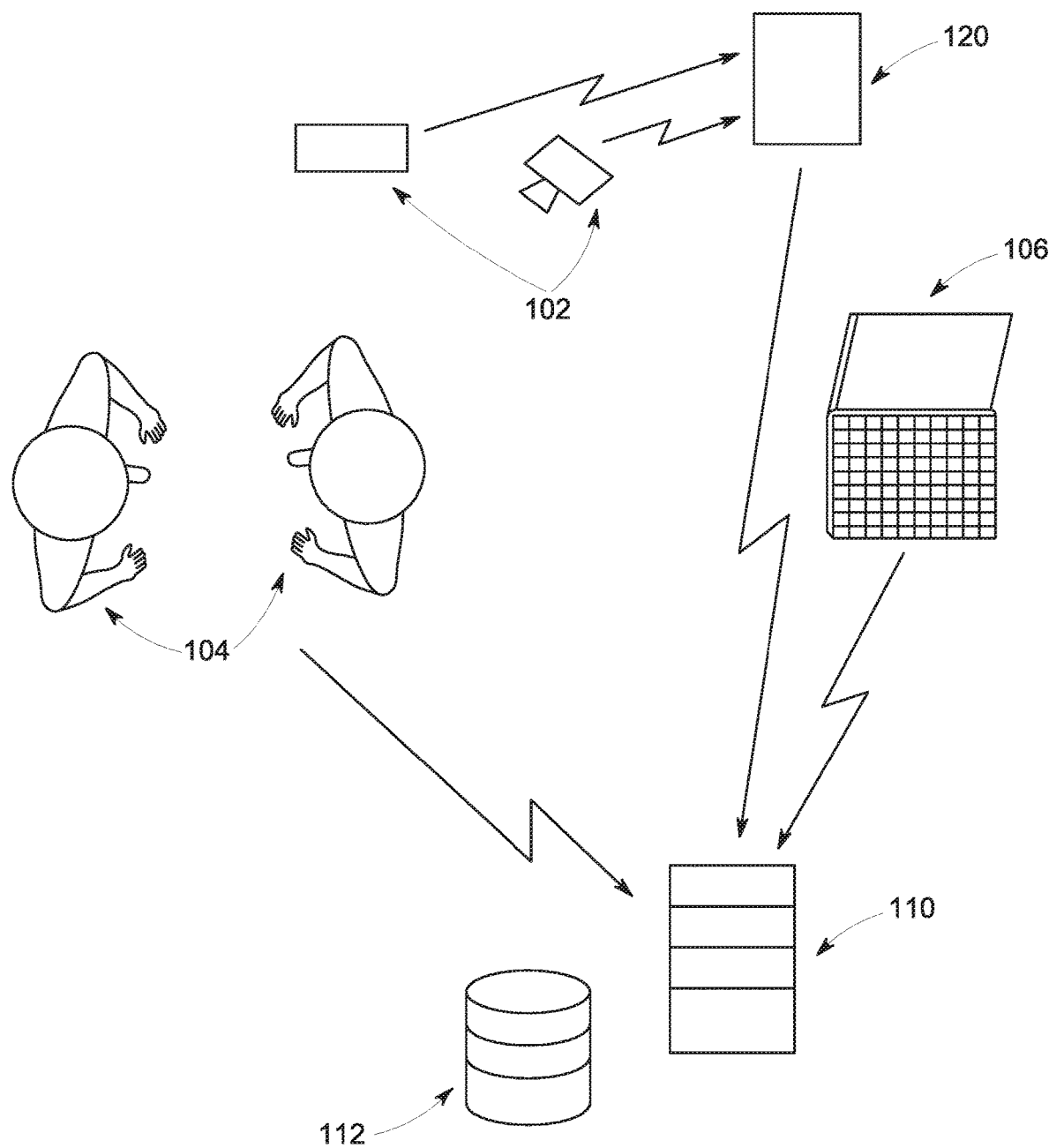
FIG. 1 is a representation of one embodiment of a system of the invention.

FIG. 1 shows one embodiment of a system 100 of the invention, which defines the elements of a transaction, and records, analyses and grades compliance with the elements and with the overall transaction. The system 100 analyses data gathered from sensors 102 (in this example depicted by a video camera and a microphone), human observations 104 (verbal, visual or written), and data gathered from existing records 106 (e.g., in a medical transaction involving a patient, gathering information from electronic medical records of the patient). A processor (defined by server 110 in this case) controlled by an algorithm defined my machine-readable code on a memory 112, analyzes and grades the data to define compliance with the one or more elements of a transaction and for the transaction as a whole. It records the analysis and grading level in a database 114 for each element in the transaction and generates reports and alerts based on the analysis and grading.

Figure 2:
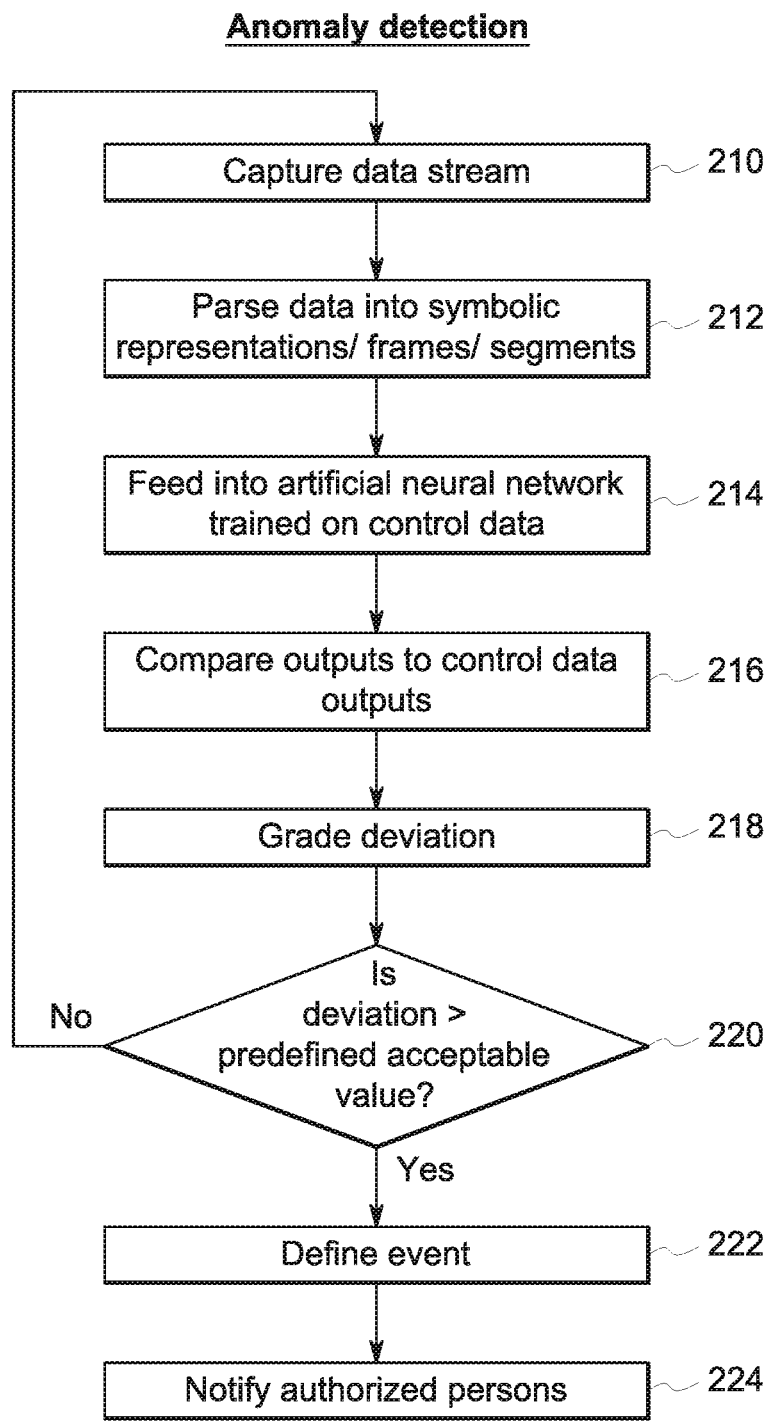
FIG. 2 is a flow chart defining the logic of one embodiment of an anomaly detection algorithm implemented in an AI system.

The logic for one embodiment of an implementation is shown in FIG. 2, which defines the analysis based on sensor data that is evaluated by an Artificial Intelligence (AI) system, in this case, an artificial neural network. Data from a sensor is captured (step 210) and is parsed into segments (also referred to as symbolic representations or frames) (step 212). The symbolic representations are fed into an artificial neural network (step 214), which has been trained based on control data (e.g. similar previous events involving the same party or parties or similar third-party events). The outputs from the AI are compared to outputs from the control data (step 216) and the degree of deviation is graded in step 218 by assigning a grading number to the degree of deviation. In step 220 a determination is made whether the deviation exceeds a predefined threshold, in which case the anomaly is registered as an event (step 222) and one or more authorized persons is notified (step 224)

It will be appreciated that the gathering of information may involve the use of standard communication systems and protocols, such as the internet. In some embodiments, sensor data 102 may be transferred by short-range communications, e.g., Bluetooth to a hub 120 connected to the server by internet.

According to one embodiment of the present system, the system records and tracks one or more elements, by recording data from sensors and/or independent observers (also referred to herein as human assessments) associated with a transaction. A typical transaction may, according to one embodiment of the present invention describe the elements making up a transaction, as well as define the basis for grading compliance with each element or with the overall transaction.

For purposes of the present invention, an assessment is defined as a subjective description of the measure of compliance with an element or with the transaction (e.g., too hot or too close), while a grading is a numeric measurement assigned to the assessment, thus quantifying it (e.g., over 75 degrees F., or within 12 inches).

An element may include any one or more of the following:
- provision by a provider of material for purposes of the transaction,
- conveyance of materials from one or more originating locations to one or more destination locations, causing the materials to physically move from one location to another without change of ownership,
- transfer of materials from one or more providers to one or more recipients, involving a change of ownership,
- physical and computational actions performed in order to provide one or more services in connection with materials,
- actions associated with the conveyance or transfer of materials,
- actions unrelated to the conveyance or transfer of materials, etc.

According to one embodiment, the system describes a transaction and observes, monitors, records, and assesses each element making up a transaction thus acting as an independent and complete description of each elements and the transaction as a whole. It may also assign a grading to the assessment, to define a measure of the degree of compliance.

This allows the assessment or grading of individual elements or the transaction to be used in generating alerts, or to serve as compliance records for subsequent review.

According to one embodiment of the system, elements of a transaction may be specified, so that in the normal course of using the system, new transactions may be created, each with its own set of elements. These may subsequently be reviewed and evaluated for compliance. Thus, a system of the invention will include:

a. A technical description that defines a transaction: defined in terms of a transaction's elements, for instance:
  1. the types of materials and instances of materials that will participate in the transaction
     an example of a type of material being a 5 mg pill of Vicodin,
     an example of an instance of a material being a 5 mg pill of Vicodin bearing the Ser. No. 15/315,534, thus uniquely identifying one instance of a 5 mg pill of Vicodin;
  2. the types of transfers and conveyances and specific instances of transfers and conveyances which will be performed in the transaction
     an example of a type of transfer being "brought by a nurse",
     an example of an instance of a transfer being "brought by nurse identified by badge RFID 9c185390";
  3. the types of participants (also referred to herein as users) and instances of participants which will participate in the transaction
     an example of a type of participant being "nurse" or "resident" or "patient",
     an example of an instance of a participant being "nurse identified by badge RFID 9c185390," or "resident 3969 of nursing home 91595";
  4. the types of services and instances of services performed as part of the transaction
     an example of a type of service being "administration of medication",
     an example of an instance of a service being "administration of medication by nurse identified by badge RFID 9c185390 to resident 3969 of nursing home 91595 on Apr. 26, 2020 at 10:00 A";
  5. additional characteristics which will constitute a valid description of the transaction, include, without limitation:
     minimum, average, expected and maximum duration of a valid transaction,
     the physical location, route, or regions involved in the transfer, conveyance or service,
     material packaging expected or required during the execution of the transaction,
     a list of substantially equivalent materials, services or participants or instances thereof which may be validly substituted in the execution of a transaction,
     the states and state transitions of any elements involved in the transaction
       examples of a state transitions of an element include:
         "nurse enters room of resident of nursing home for morning rounds"
         "resident of a nursing home becomes unresponsive to voice prompts"
       examples of a state transitions of an instance of a element of a transaction include:
         "nurse identified by badge RFID 9c185390 enters room of resident 3969 of nursing home 91595 on Apr. 26, 2020 at 9:58 AM"
         "resident 3969 of nursing home on Apr. 26, 2020 at 10:04 AM becomes unresponsive to voice prompts";
     phase changes of materials involved in the transaction.

b. Transaction-specific sources of evidence: Data which will be used to assess or grade the outcome of the transaction, examples of which include, without limitation:
  1. A nurse report which affirms medication was administered,
  2. the patient report which affirms medication was administered,
  3. the data stream from a sensor, e.g., a radio frequency (RF) array, video camera, or other image capture device, which confirms medication was administered.

c. Global sources of evidence: In addition to the data from transaction-monitoring sources discussed above, validating data may be obtained from global data sources, e.g.,
  1. visual
     2D radar array
     3D video camera
  2. audio
     Stereo audio
  3. other perceptual e.g. temperature of patient or room, verbal characteristics of patient
     temperature sensing by thermal camera a radar array recording of administration of medication,
     an audio recording of administration of medication,
     a video recording of administration of medication,
     a record of the time the nurse reported the medication was administered and related to the time the video monitor determined the medication was administered,
     a record of the time the patient reported the medication was administered and related to the time the video data determined the medication was administered, d. Gradings, reports and records based on the sensor, and human-generated data: These may be used to assess or grade the outcome of a transaction. These may be captured and made available in one or more of:
  1. local storage using SSD or RAID array,
  2. streaming to cloud via internet connection,
  3. storage as rows in tables in a relational database, with those tables having normalized relationships, e. Algorithm/Artificial Intelligence system implementation: defining the assessment and grading algorithms and their inputs and outputs (which may depend on the type of data, the granularity of the data and the way it is processed), examples of which include, without limitation:
  1. neural network type, such as Feedforward, Radial Basis, or Convolutional,
  2. binary or scalar outputs,
  3. number and types of inputs, Thus, according to one embodiment of the invention, the system defines the transaction and its components and then verifies compliance, by:
  performing an assessment and grading of components of the transaction e.g. of elements
  performing an overall assessment and grading of the entire transaction
  generating reports about the transactions
  generating alerts regarding aspects of the transactions, such as but not limited to:
    a. the semantic or subjective outcome of an assessment,
    b. the numeric value of a grading.

Components of a Transaction:

It will be appreciated that some of the elements of a transaction will be identifiable ahead of time and form the basis for verification of a transaction or an event. However, some elements may only become evident during a transaction, e.g. by being captured in the course of a transaction or forming part of an independent transaction. This may include sensor data, physician diagnosis (including electronic medical records (EMR)). These may serve to confirm compliance with a facet of a transaction or may trigger a new transaction, e.g., a patient falling and breaking a hip.

Each transaction may therefore be defined in terms of the elements involved and the standards or rules that will determine whether an element was completed to satisfaction, in order to provide reports and assessments of subjective compliance and objective compliance (based on a grading scale). The elements defining a transaction may include, but are not limited to, one or more of the following items:

1. parties to the transaction:
    participants with an active role in the transaction, such as
        person, device or other agent which delivers, transfers or conveys a material and/or service(s)
        person, device or other agent who receives the material or benefit of the service(s)
        person, device or other agent which performs a service
2. parties who do not play an active role in the execution of the transaction but may have an interest in or may passively provide support for the transaction, e.g.,
    independent observers, such as a certifying authority, for example a notary public
    regulatory agencies such as the FDA or USDA
    representatives of legal firms
    insurance companies
3. the material(s) which are conveyed between or by parties to a transaction;
4. date(s) and time(s) of execution of the transaction, and of the transfer or conveyance. There may be multiple dates and times involved, e.g. start, departure, arrival, start times, end times, etc.
5. Conditions and terms of service:
    a description of the service(s) performed or to be performed
    a description of the conditions which parties agree constitute valid performance of the service(s) or constitute compliance with a valid element and/or valid transaction.
    a description of method(s) used to convey and/or transfer the material or perform the service(s)
6. the proof, verification or evidence used to substantiate the veracity of any or all aspects of the transaction. This may include:
    a. feedback from the recipient confirming the successful or acceptable execution of the transaction, for example the receipt of the material or performance of services;
    b. satisfaction level of the recipient(s) to the transaction, as a result of the execution of the transaction, such as the transfer of materials or performance of the services;
    c. observations formed using the output from sensors and/or independent observers of components of the transaction, e.g.,
    d. an electronic image of a document signed by a notary public notarizing the credentials of a party
    e. a raw or compressed recording of the data from an array of RF sensors used to monitor the administration of medication by a nurse to a patient.

According to one aspect of the present invention, the data gathered to show compliance, is correlated between two or more observations within a transaction which corroborate and constitute proof of compliance, or correlations between other data and events observed or recorded in order to substantiate the veracity of one or more aspects of a transaction and support evaluation, grading and assessment, and determine the satisfaction of conditions.

For example, the intent, sentiment and meanings of the words spoken during the transaction may be correlated with the actions recorded in order to establish the sufficient performance of services. Multiple components may thus be considered when assessing and grading the transaction.

In one embodiment, an assessment and grading is performed based on each of these components and observations separately, and the results combined to yield a positive or negative rating.

In another embodiment, corroboration of data from one sensor or observation with at least one other sensor or observation, is first sought before compliance is assessed and a grading applied based on the strength of the data. For instance, a confirmation by a patient that they received their medication may have a greater weighting factor than a nurse's compliance statement (assuming the patient is not suffering from cognitive decline).

As is evident from the above example, one implementation of the system of the present invention is in the medical field. For example, the system may record, assess, grade, and provide notification of completion and degree of compliance with a transaction in which a nurse administers medication to a patient. The nurse conveys and administers the material e.g., a drug to a patient. The material may be administered as a dose of medication, and the recipient is the patient receiving the dose of medication. Instead of relying purely on the participants' statements, the proof may be determined by means of sensors which observe the parties during the transaction, capturing data over a period of time rather than at one moment in time, which may capture only one element of the transaction, e.g. the isolated step of opening a pill pack. The opening of the pill pack may be only one element in a transaction that includes a nurse, a patient, a drug, a time, an administration—all of which provide opportunity for validation and corroboration of the various steps constituting the overall transaction).

Compliance with the transaction elements may include independent observations about the conveyance, or the performance of services. It may also integrate indirect parameters, such as the behavior, i.e., physical and emotional reactions of the parties thereto, both within the timeframe of the transaction and thereafter. For example, several minutes after the taking of a pill, the patient may go into convulsions, which falls outside the time-frame of the transaction but is nevertheless relevant to the question of satisfactory compliance with the transaction of conveying and administering the medication.

Figure 3:
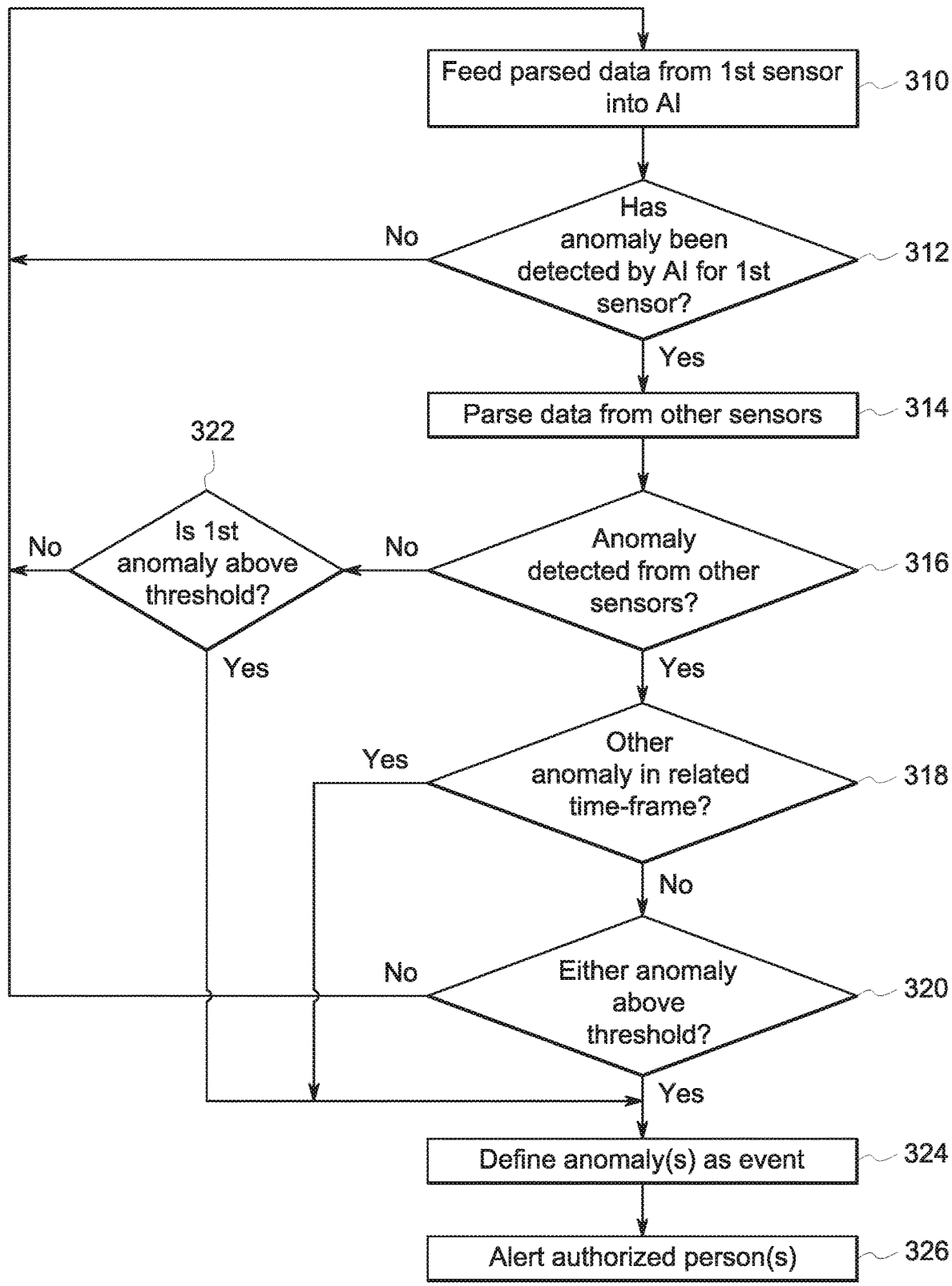
FIG. 3 is a flow chart defining the logic of one embodiment of an anomaly detection and corroboration algorithm implemented in an AI system.

One embodiment of the logic in making a determination based on grading of an anomaly and/or corroboration between sensors is shown in FIG. 3.

Parsed data from a first sensor is fed into an AI system (step 310). Insofar as an anomaly is detected in the data (step 312), this is corroborated against data from at least one other sensor by parsing data from the other sensors that are involved in the particular implementation (step 314). In step 316 a decision is made whether any of the other sensor data shows up an anomaly, in which case it is compared on a time scale whether the second anomaly is in a related time frame (which could be the same time as the first sensor anomaly or be causally linked to activities flowing from the first sensor anomaly) (step 318). If the second sensor anomaly is above a certain threshold deviation (step 320) or, similarly, even if there is no other corroborating sensor data, if the anomaly from the first sensor data exceeds a threshold deviation (step 322), the anomaly captured from either of such devices triggers an event (step 324), which alerts one or more authorized persons (step 326).

Examples of practical applications of the compliance monitoring and notification in accordance with this invention include:

- A son calls his mom in the nursing home, mom complains she didn't get her medication. Son would like a way to know if a medication nurse came in, and determine with certainty if the nurse delivered or administered the medication.
- The CEO of a nursing home would like alerts when nurses in his employ did not administer medication correctly, or did not do so in a timely manner, or did not following the required procedures when administering the medication.
- The owner of an oil drilling platform would like a summary report and alerts when safety procedures are violated during the operation of the drilling platform by the operators.

In order to record a material conveyance and performance of services and to verify transfer, the present invention includes independent observation and correlation of those observations to yield an assessment and grade. The observations include objective data, in the form of one or more sensors which observe the conveyance of material and performance of services and record them independently of the conveyance and performance themselves. It also includes capturing of data from non-sensor sources such as a nurse's medication administration records, in order to correlate the findings of each independent observation and source yielding an assessment and grading of each facet of interest, and creating an overall assessment and grade for the transaction to define whether or not there was adequate compliance and where the shortfalls occurred for future improvement.

The sensors may cover specific locations or multiple locations, with regions covered by some sensors overlapping with others to facilitate corroboration of data. examples of sensors include, without limitation:
 a. radio-frequency sensor arrays
 b. video or still photography cameras
 c. streaming or still thermal cameras
 d. monaural or stereo microphones
 e. sonar sensors
 f. ultrasonic sensors
 g. subsonic sensors One aspect of compliance with a transaction, in accordance with the present invention, involves validating the identify of parties to the transaction, and verifying what materials or devices were involved. In order to identify participants and/or materials, different validation methods may be adopted, including:
 a. RFID tags
 b. bar codes
 c. retina scans
 d. facial recognition
 e. voice print
 f. tattoos (visible or invisible)
 g. genetic code
 h. cameras (various frequency spectrums depending on needs, penetration requirement, privacy) behavioral evaluation (e.g., of a person's gait, or of their manner of speaking)

These sensors, to the limits of their abilities may be used to detect and record the presence, movements, and actions performed by the participants and materials involved before, during, and after the performance of the conveyance or execution of services, as well as their orientations, trajectories and states of the participants and materials. Recording the before-and-after information prior to the beginning of the transaction and after the end of the transaction provides additional data for correlation and may yield insights as to the successful or unsuccessful conveyance or performance of services.

For example, as mentioned above, in the case of a nurse administering medication, the conveyance and performance may appear successful at first, but after the nurse leaves (when the transaction is apparently complete), if the patient exhibits signs of distress, this may be taken into account to assess whether performance was successful, since the undesirable outcome may have been due to a discretionary action or decision (amount or type of medication) performed during execution of the transaction by the nurse.

After or during collection of the data for the observation, the data will be fed into one or more algorithms or artificial intelligence networks in parallel and/or in sequence, for validating compliance with all elements (also referred to herein as events) of a transaction, identifying emergency events that require triggering an alarm to notify one or more people, and for grading elements. the AI system(s) are trained on each of the critical elements of a transaction to analyze similar types of data in order to arrive at the assessment or grading of each element.

In one embodiment, before feeding the data into the algorithm or AI network, the raw data from the sensors is converted into one or more symbolic representations in order to facilitate a more accurate, or more efficient interpretation by the algorithm or AI network. This may include passing the data through one or more parsers to extract specific types of information from a data stream.

The data is also converted into a format more easily interpreted by humans e.g. multiple sensor readings are displayed against a common timeline (clock).

Examples of symbolic representations include, without limitation:
 1. in a photo, video, thermal imaging, radar array or other data snapshot or data stream: parsing the objects and their elements, with the goal of identifying by name, type or other characterization, the presence of, actions pertaining to, and/or interaction between participants, materials, services or other objects.
 The purpose is to identify, as much as possible, the characteristics of each object, such as the amount of material, and performing motion tracking and calculating trajectories of each object through 3D space, and assessing the state of each (for example the presence of convulsions, or potential emotional state of a participant through facial recognition or tone of voice, or tracking the phase or phase change of matter involved in the transaction). By extracting these various parameters, the present system creates a chain of evidence based on the use of multiple sources of evidence e.g. multiple sensors and human statements.
 2. In the recorded or live audio, ultrasonic, subsonic or sonar data, parsing of such data serves to extract details about the presence of and interactions between objects, actions, emotional states, intent, and subjective intent, such as through vocal inflection.

In the recorded or live subsonic vibrations, this may for example identify collisions, falls, impacts, or other events which may indicate or substantiate the presence of or interaction between objects or participants. Multiple sensors covering an observed region may thus each identify actions performed, collisions, falls, impacts, or other events of significance, and corroborate each other's data.

The issue of monitoring phase changes was discussed above. This may be observed in the data as follows:

An object which has been identified in symbolic form may suddenly or gradually disappear from the observed data stream or observed environment or setting. A second object identified in symbolic form suddenly or gradually appears from the observed data stream or observed environment or setting in a location that can be interpreted as predictively related to the previously disappearing symbol. Provided a known transformation function can be applied to the first symbol which predicts that upon application of the transformation function the first symbol would disappear in current form and one or more symbols would then emerge in approximate spatial, temporal, thermal and density relationships having properties predicted and expressed by the transformation function, the overall observation would demonstrate sufficient coherence to support the assertion that the first symbol has transmuted into one or more subsequent symbols.

As discussed above, in addition to objective assessments of compliance with elements of a transaction, the present invention also includes recording subjective data, e.g., the participants' assessment of the transaction during and/or after the execution of the transaction. In one embodiment this includes the ability for participants to later modify their assessment should they wish to do so, for example upon discovering the material to be fraudulent or a service having subsequent negative consequences. This can provide further data for overall assessment of the success or failure of the transaction, or any facet thereof.

An immutable record may be kept of the transaction and subjective assessments, with subsequent changes by participants treated as additional records, allowing comparison between assessments over time.

In one embodiment, the system will be employed to determine when medication has been successfully and appropriately administered to a patient by a nurse and graded according to generally accepted or specified nursing principles and standards. The participants may be identified using RFID, voice print, and/or facial recognition. The motions and interactions undertaken by the participants during conveyance and administration of the medication will be monitored by 3D video, 3D radar and 3D sonar arrays, with the video being used to identify participants, objects and their position in space and to read labels on the medication using optical character recognition, the radar array being able to detect presence of masses in space and aspects of their internal composition, as well as their position and orientation, the sonar array being able to identify exterior shapes and provide an outer shell of textures and surfaces for mapping onto the 3D video and 3D radar array data to create a complete 3D-picture of the participants and materials over time in 3D space.

Some sensors can be permanently present in the patient's room, while some are brought in as part of the cart or dispensing tray for the medication or drug etc. Statements made by the participants before, during and after the transaction, will be recorded and parsed for meaning, intent, and emotional state using sentiment analysis based on speech patterns, wherein veracity may be determined by voice stress analysis. Such statements may be assessed passively or intentionally elicited by the observing sensors and systems by, for example, annunciating a statement or query via a speaker in order to observe, collect, record, analyze and gauge response. These passive and active prompts include verbal, image-based, and physical prompts that may be issued in any form, such as by speaker, video screen, text-based interface, web page, etc., or may be the result of interacting with a participant in the transaction (also referred to herein as a user), e.g., substance injection, which elicits a sensory or physical or emotional stimulus. The response of the user to such stimuli may be picked up by sensors or actively solicited from the user, e.g. by feedback in any form of text or voice. In one embodiment, the user may be prompted by a voice device enquiring about the satisfaction of the user, how they are feeling before and after an event, the system using voice recognition to assess and grade the feedback of the user. This allows both the emotional state of the user to be assessed and transaction compliance to be determined.

For example, after a nurse has completed the administration of medication to a user and has left the room, a voice bot prompts the user via a speaker, enquiring of the patient their level of satisfaction with the administration of their medication, asking how they were feeling beforehand, and how they are feeling now that they have received their medication. The patient's verbal response or lack thereof is analyzed by parsing the data and analyzing for assessment and grading, as described in further detail below.

In one embodiment, all medication is conveyed within an automated dispenser which requires biometric authentication by the patient and premeasures the dose according to an electronic prescription schedule, and which independently records the administration of the medication, e.g., on a blockchain in order to create an immutable, transparent, private and cryptographically verifiable record. An example of such a device may be a pill box which opens with the patient's thumbprint, or a medication inhaler with a lip-print biometric lock. Another example may be a needle or microneedle injector with biometric authentication, or a dermal patch dispenser or sublingual strip dispenser with a biometric release.

In general, the data streams from the sensors will be fed into parsers of types appropriate to individual and combined streams to generate symbolic representations of the components in each stream or combinations of streams, and generate a higher-level symbolic representation of the actions, conveyances, transfers, materials, services, participants and all other components pertinent to the transaction.

As an example of the process for converting a raw data stream into symbols which can be used to feed a neural network to generate an assessment, an audio data stream of a conversation between nurse and patient is passed into a parser which has been trained to scan the entire waveform, identify the characteristics of a singular voice in the recording, then rescan from the beginning and output separate data streams, each one containing only those sounds emitted by a singular voice. In each output stream the relative timing of the sounds is retained in relation to the sounds of all voices recorded, permitting later correlation of the sounds and utterances between voices.

Each single-voice data stream is then parsed further by being fed into a generalized phoneme recognition neural network which parses the raw waveforms into a base symbolic form, for example, the 44 phonemes of the English language. After phonemic parsing for a single voice, these symbols are grouped into potential parts of words, entire words, or groups of words, where the groups are defined by a beginning and ending gap in time. These phoneme groupings are then fed into a word-identification neural network to recognize the phoneme groups as words or parts of words.

In a parallel stream of processing, each single voice track is fed into a cadence and intonation parser trained to recognize beginning and ending of sentences and to generate groups of phenomes identified as individual sentences, categorized into statements and questions. For example, the beginning of a sentence usually begins after a slight pause in speech, and the frequency of the final few open (vowel-like) phonemes of a sentence usually have predictable qualities such as gradually descending in average audio frequency, and in the case of a question the average audio frequency of the final vowel-like phoneme rises.

Once potentially word and sentence phonemic groupings have been recognized, the words along with alternative words (in case of mis-identified words), are fed into another parser to identify important parts of speech, such as nouns, verbs and adjectives. This can be accomplished by a look-up against a dictionary of potential combinations of phonemes which, for instance, constitute each noun, verb and adjective in the English language dictionary, supplemented with a reference including localized slang and specialty specific terms such as those used in nursing.

These symbolic forms can then be fed into neural networks trained to apply common rules of grammar to identify the subject, object and predicate of each sentence.

This process can be further refined over time, re-analyzing the input waveforms and gradually improving the accuracy of the subsequently derived symbols into a highly-accurate salient set of symbols which, when processed by neural networks trained using well-known rules of speech and dictionaries of meanings, infer the meanings conveyed by each discourse, and the intent and even the emotional state of each participant.

Finally, the a single-voice analyses are cross-correlated with the single-voice analyses of the other participant(s) in order to assess qualities of the interaction, such as the level of defensiveness in a participant, presence and level of emotional reactions such as frustration, level of understanding of information conveyed, degree of confusion, or expression and degree of concern expressed by a participant. This also allows emotional changes to be assessed over time e.g. prior to administration of medication, during administration in the presence of the nurse, and afterwards once patient is alone.

In one embodiment, these higher-level symbolic representations such as level of concern, degree of confusion or understanding, which medication and dosage was administered, and how that administration was emotionally received will be fed into several deep neural networks, each of which was previously trained to assess one element, e.g. of a similar administration scenario, of a similar medication, or in a similar setting, each yielding a score for the assessment and grading of that element.

The feedback from each participant, e.g., nurse and patient, will likewise be parsed into components which convey information and sentiment about an element of the transaction, and sentiment about overall satisfaction with the performance of the transaction, and assessment and grading as to its level of completeness, quality of performance, and overall success or failure.

In one embodiment, the assessment includes a subjective element where the patient is provided with a device such as a smartphone or tablet configured with a software app, or a dedicated device displaying red and green buttons to enable the Participant to indicate a successful or unsuccessful transaction and a one-to-five star interactive indicator for the participant to input their level of satisfaction of performance associated with the transaction or with various elements of a multi-element transaction. The device may include the ability to input a thumbprint or PIN to positively identify the participant. This information can be recorded on a blockchain in order to store the information in an immutable, transparent, private and cryptographically verifiable manner.

The subjective feedback is likewise fed into neural networks trained to derive an assessment and grading score for each element.

Objective data obtained from the nursing facility's Patient Medication Administration System can also be fed into an algorithm or neural network to generate an additional source for evaluation.

Similarly, data obtained from biometrically controlled medication administration devices can be fed into an algorithm or neural network to generate an additional source for evaluation.

All element assessments and grades are then fed into a final neural network, which is used to create a combined overall assessment and grading of the transaction and an overall yes/no determination as to the successful completion or failure of the transaction.

The results of the yes/no overall determination and the results of the contributing sub-assessments and grades can be recorded on a public or private blockchain in order store this information as a private, immutable, transparent, and cryptographically verifiable record. This blockchain may then be queried by concerned individuals such as the patient's family members, or employees of the business, or regulatory or compliance agencies in order to monitor and follow up as needed or desired, or used in a court of law for evidence of compliance or malfeasance.

During or after the assessment and grading of the entire transaction the system may then generate alerts and provide reports to registered, required or interested parties, such alerts being generated by text, voice, email, or any other alert mechanism. The reports may be made available using commonly employed practices such as via a web page over the internet on a PC or handheld, or via generalized or specialized reporting software.

All parts of the process are recorded in logs for later reference and review and potential problem determination and improvement.

While the present invention has been described with respect to particular embodiments and implementations it will be appreciated that the system of the invention can be implemented in different configurations, for different purposes, using different sensor and user data, and based on different compliance parameters, without departing from the scope of the invention.

What is claimed is:

1. A system for validating transactions that involve interactions with a user, comprising
   a database for storing elements of a transaction, details about the participants, and compliance details for compliance with the elements of the transaction, at least two sensors for gathering transaction data between at least a first time and a second time, a processor, and a memory that includes machine-readable code defining an algorithm executable by the processor for analyzing data, including data from at least a first sensor to verify compliance with the compliance details and for corroborating compliance or lack of compliance by analyzing data from at least a second sensor for corroboration of the data from the first sensor.

2. The system of claim 1, wherein the algorithm defines an artificial intelligence (AI) system configured to identify anomalies in the data captured by at least one sensor.

3. The system of claim 2, wherein the anomalies in the data include at least one of, anomalies in the data captured from a sensor over time during a transaction timespan, anomalies in sensor data compared to prior data captured for the user for previous transactions, and anomalies in sensor data compared to similar sensor data gathered under similar conditions for other users.

4. The system of claim 3, wherein the transaction timespan includes timespans before the first time and after the second time.

5. The system of claim 1, wherein the data captured for analysis includes data provided by people, including one or more of: the user, other parties to the transaction, and parties peripherally associated with the transaction.

6. The system of claim 5, wherein the machine-readable code includes logic for capturing and storing the data provided by people, including at least one of documentation and recordings related to the transaction.

7. The system of claim 6, wherein the sensor data and data provided by people includes visual data, audio data, and other perceptual data.

8. The system of claim 7, wherein the sensor data includes one or more of radar array recordings, audio recordings, video recordings, time records of events, compliance data captured by systems, temperature data, radio-frequency sensor array data, video and still photography camera data, streaming and still thermal camera data, monaural and stereo microphone data, sonar sensor data, ultrasonic sensor data, and subsonic sensor data.

9. The system of claim 1, wherein the machine-readable code includes logic for authenticating one or more people forming part of a transaction, the system including data captured from one or more of, image capture devices, RFID tags, bar codes, identification cards, retina scans, facial recognition, voice print, visible or invisible tattoos, and genetic code.

10. The system of claim 1, wherein the transaction data captured by the system includes one or more of: types of materials involved in the transaction, quantity of material, any changes to those materials during the transaction, and the tracking of the movement of such materials.

11. The system of claim 1, wherein the database includes one or more of: local storage using an SSD or RAID array, a distributed database or cloud system, and in a relational database.

12. The system of claim 2, wherein the machine-readable code includes logic for defining the level of compliance with an element of a transaction or a transaction as a whole and for generating an alert in the event of the compliance value falling below a defined value or based on the detection of an anomaly.

13. The system of claim 2, wherein the transaction data includes one or more of: facial expression, body posture, body movement, and vocal attributes data, and wherein the AI system is configured to assess the demeanor or emotional state of one or more participants in the transaction.

14. The system of claim 13, wherein the transaction data from the sensors is parsed to define symbolic representations to facilitate a more efficient interpretation by the AI system, wherein the conversion of sensor data into a symbolic representation includes passing the data through one or more parsers to extract specific types of information from a data stream.

15. A method of verifying transactions involving interactions with a user, comprising defining the elements of a transaction, identifying the compliance details defining compliance with one or more of the elements of a transaction, capturing data from sensor- and human-provided data sources relating to said transaction, and using an algorithm to analyze the data, verify compliance with one or more elements of a transaction, and corroborate the compliance or lack of compliance by comparing two or more of the data sources of said transaction.

16. The method of claim 15, wherein the algorithm comprises an AI network, and includes logic to compare data from multiple data sources for the same time frame or related time-frames.

17. The method of claim 16, wherein the analyzing of the data includes identifying at least one of: the physical state, and the emotional state of one or more of, the user, and other parties involved in the transaction.

18. The method of claim 16, further comprising defining emergency situations based on corroborated anomalies and lack of compliance, and notifying one or more parties in response to the emergency.

19. The method of claim 18, further comprising keeping a record of transactions and details about users and other parties to transactions, and generating reports in response to one or more of: identification of compliance or non-compliance with elements of a transaction, anomalies detected in the data from one or more of the data sources, defined events, and authorized requests.

20. The method of claim 18, further comprising defining the degree of compliance according to a grading scale.

* * * * *